United States Patent [19]

Janick et al.

[11] Patent Number: 4,545,147

[45] Date of Patent: Oct. 8, 1985

[54] **ASEXUAL EMBRYOGENESIS OF CALLUS FROM *THEOBROMA CACAO* L.**

[75] Inventors: Jules Janick; Halina M. Kononowicz, both of West Lafayette, Ind.

[73] Assignee: Purdue Research Foundation, West Lafayette, Ind.

[21] Appl. No.: 521,077

[22] Filed: Aug. 8, 1983

[51] Int. Cl.⁴ .............................................. A01G 1/00
[52] U.S. Cl. ...................................................... 47/58
[58] Field of Search ............................................ 47/58

[56] References Cited

U.S. PATENT DOCUMENTS

| | | | |
|---|---|---|---|
| 4,204,366 | 5/1980 | Janick et al. | 47/58 |
| 4,291,498 | 9/1981 | Janick et al. | 47/58 |
| 4,301,619 | 11/1981 | Janick et al. | 47/58 |

Primary Examiner—Robert E. Bagwill
Attorney, Agent, or Firm—Sughrue, Mion, Zinn, Macpeak, and Seas

[57] ABSTRACT

A method for growth, development and maturation of cacao embryos produced from the callus of *Theobroma cacao* L., and product of such method.

9 Claims, 18 Drawing Figures

ASEXUAL EMBRYOGENESIS OF CALLUS FROM *THEOBROMA CACAO* L.

FIELD OF THE INVENTION

This invention relates to a method for in vitro growth of cacao embryos from the callus of *Theobroma cacao* L., and the product of such method.

BACKGROUND OF THE INVENTION

There are two general patterns of in vitro embryogenesis: *direct* initiation from differentiated tissue, and *indirect* initiation via a callus intermediary. Direct embryogenesis proceeds from embryogenic-determined cells (Kato and Tukeuchi, 1966). Indirect embryogenesis requires dedifferentiation of embryogenic-determined cells, callus proliferation, and differentiation of embryogenic cells (Sharp et al., 1980). In vitro asexual embryogenesis occasionally occurs in the absence of exogenous hormones (Halperin and Jensen, 1967), but in most cases requires the manipulation of hormonal balance in the medium (Gamborg 1970).

Direct somatic embryogenesis from immature zygotic cacao embryos proceeds by two distinct patterns: a "budding" process in which cells of the hypocotylary epidermis develop to mimic the normal stages of embryogenesis including the development of a suspensor (Esan 1977, Pence et al. 1979, 1980) and a "nonbudding" process where a differentiation of embryos is from internal meristematic cotyledonary tissue. Direct somatic embryogenesis occurs at low frequency on basal medium alone but a combination of auxin (IAA, NAA, or 2,4-D) and coconut water stimulates the embryogenic process (Pence et al. 1979, 1980). The "budding" process continues from asexual embryos and some cultures continue to proliferate in this manner in a hormone-free medium.

Cacao callus has been initiated from various tissues including leaves (Pence et al., 1979; Searles et al., 1976), fruit (Searles et al., 1976), seedlings (Hall and Collin, 1975), and zygotic embryos (Hall and Collin, 1975; Tsai and Kinsella, 1981; Pence et al. 1979), but the only organized development from callus was limited to roots (Hall and Collin, 1975; Pence et al. 1979). This invention describes the process of asexual embryogenesis via callus tissue in *Theobroma cacao* L., procedures for the induction of embryogenic callus, and the histology of somatic embryogenesis. The asexual embryos so produced may then be grown for utilization as a cocoa butterlike product.

SUMMARY OF THE INVENTION

Callus tissue of *Theobroma cacao*, processing embryogenic-competence occurred spontaneously from 2 clones of asexual embryos proliferated in vitro by hypocotylary budding. Asexual embryogenesis via callus occured at low frequency in a hormone-free basal medium. High concentrations of 2,4-D plus coconut water (CW) stimulated callus production and suppressed embryo production. Maximum frequency and intensity of embryogenesis occured at $10^{-3}$ to $10^{-2}$ mg/liter 2,4-D. Embryos originate from meristematic tissue at the periphery of callus clumps. Asexual embryos during development either remain embedded in the callus or are connected through suspensor-like structures.

DETAILED DESCRIPTION OF THE INVENTION

Culture media

Figure 1:
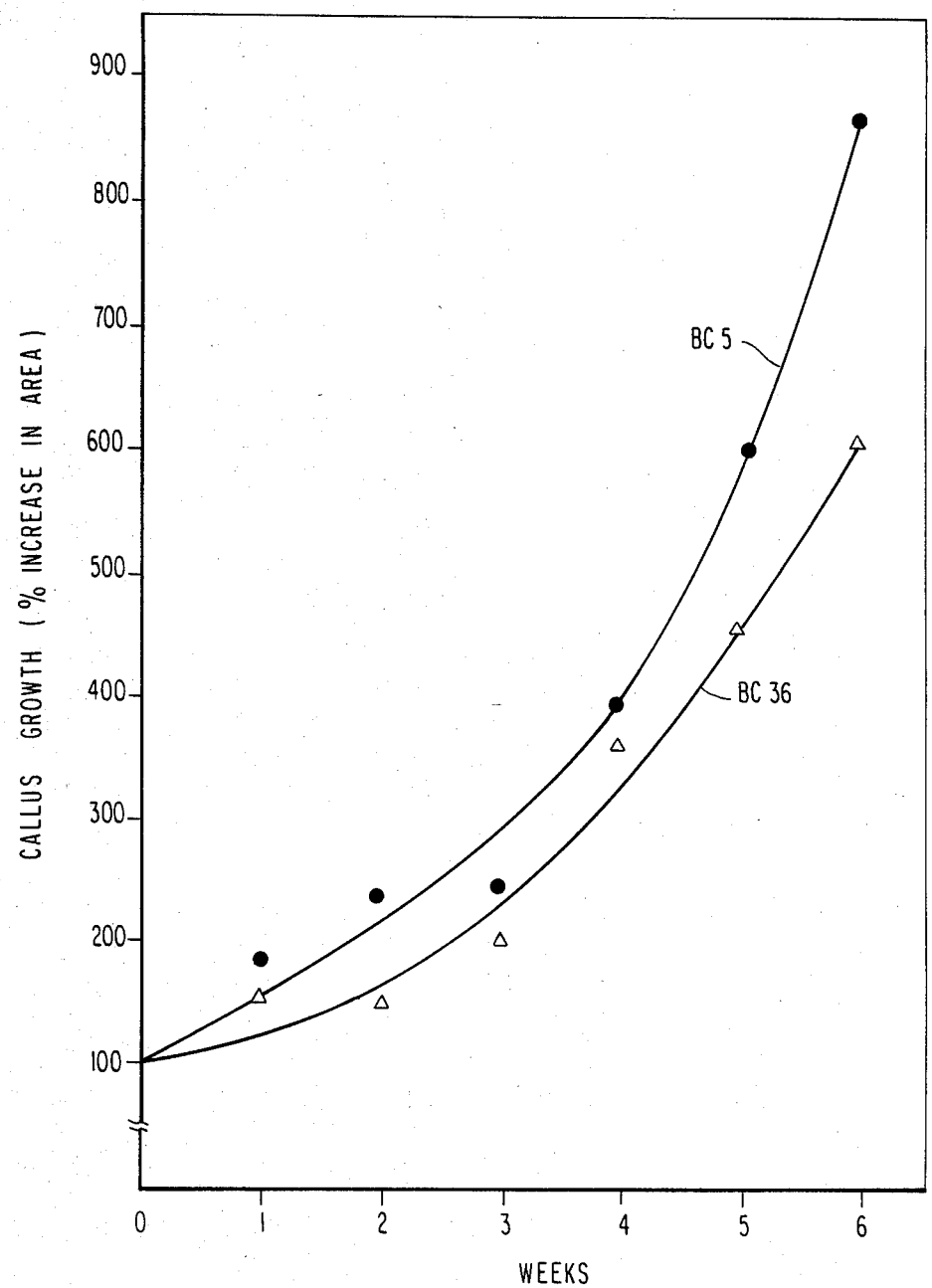
FIG. 1 is a graph showing the time course of callus growth of clone BC 5 and clone BC 36 in basal medium.

Procedures for the culturing of asexual embryos direct from immature zygotic embryos were described previously in U.S. Pat. Nos. 4,204,366, 4,291,498, and 4,301,619. The basal medium (in mg/liter) consisted of Murashige and Skoog (1962) salts, consisting of 0.1 thiamine HCl; 0.5 pyridoxine HCl; 100 i-inositol; 0.5 nicotinic acid; 2.0 glycine; 1000 casein hydrolysate;

15000 sucrose; and 8000 Bacto-agar. Where described, media were supplemented with various concentrations of 2,4-D from 0 to 2 mg/liter and/or coconut water (100 ml/liter). The medium was sterilized by autoclaving after adjusting the pH to 5.7.

Plant material

All experiments were carried out on 2 clones, BC 5 and BC 36, derived from zygotic embryos as described by Pence et al. (1979, 1980). These 2 clones spontaneously form callus through cotyledonary tissue when cultured on basal medium. The quality of the callus was divided into 2 kinds; (1) friable, ranging from white to pale yellow and (2) soft brown, often covered with a gelatinous substance. Previous experience indicated that the soft brown callus was nonembryogenic. The friable white-yellow callus from BC 5 and BC 36 were separated from the cotyledonary tissue and subcultured on fresh media. The stock callus cultures were grown in glass jars (7 cm×5.5 cm diameter) containing 15 ml basal medium and placed under low intensity illumination (25–100 mol sec $^{-1}$m$^{-2}$) from Cool White fluorescent lamps per 16 hr daily at 26° C. Callus was subsequently subcultured at 6 week intervals.

The friable yellow callus tended to subdivide into small portions. Pieces of callus about 10–15 mn$^2$ was used to initiate experiments. Callus growth was measured at 7 day intervals for 6 weeks by calculating area (Dale and DeAmbione, 1979) derived from two diameters, the largest ($D_1$) and one perpendicular to it ($D_2$). Callus area=($D_1$ $D_2$)/4.

The number of embryos initiated from callus was counted under a stereoscopic microscope 6 weeks after transplantation. The frequency of embryogenesis is presented as a percentage of callus culture producing somatic embryos relative to the control. The degree of intensity of embryogenesis is expressed as the average number of embryos per culture relative to the control.

Preparation of samples for histological examination

Callus sections were made from cultures 3 weeks after transferring on fresh basal medium. Callus tissue with embryos at different stages of differentiation was fixed in FAA (formalin;galacial acetic acid;ethanol, 5:5:90, v/v/v), passed through ethanol-tertiary butanol series, and embedded in Paraplast. Sections, 5–7 m thick, were stained with safranin and fast green or with Mayer's haematein. Cell sizes were determined with an ocular micrometer.

Results

Pale yellow callus from cotyledonary tissue grown on basal medium of BC 5 and BC 36 proved capable of continual growth when transferred to fresh medium. The most rapid rate growth was achieved after 2 or 3 weeks (FIG. 1). Callus remained yellow and friable with an irregular surface, up to 6 weeks. New white cell masses continually appeared around the periphery of the yellow callus in contact with the media but, after 6 weeks unless recultured, the callus mass turned brown and the surface appeared dry. A brown gelatinous callus often arose anew on the top surface.

The effect of 2,4-D and CW on callus growth

Figure 2:
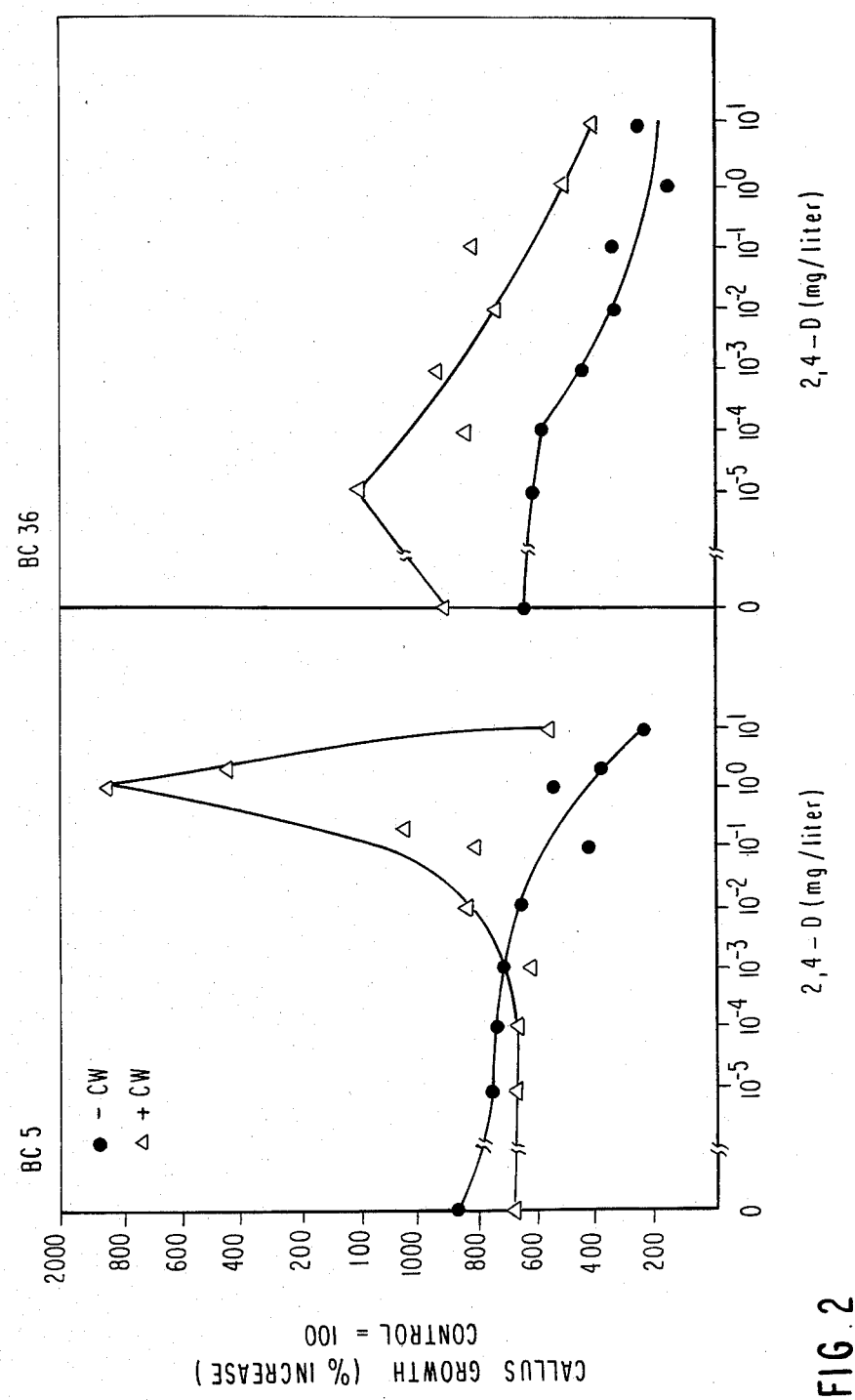
FIG. 2 is a graph showing the effect of 2,4-D and CW on callus growth of clone BC 5 and clone BC 36 after six weeks.

The effect of 2,4-D with or without CW on callus growth of BC 5 and BC 36 is shown in FIG. 2. In both clones, callus growth was unaffected by 2,4-D without coconut water in concentrations lower than $10^{-3}$ mg/liter, but growth decreased with increasing concentrations above $10^{-2}$ mg/liter. About 1.0 mg/liter callus turned brown.

Callus growth responded differently to 2,4-D in the presence of CW. Callus growth of BC 5 increased rapidly from $10^{-3}$ mg 2,4-D and reached a maximum at 1 mg/liter. This fast-growing callus was bright yellow, friable, and appeared homogeneous without any evidence of embryogenesis. Callus formed in response to CW+2,4-D above 2 mg/liter turned brown and died. With BC 36, callus growth was always greater in the presence of CW and was maximal at $10^{-5}$ mg/liter 2,4-D.

Effect of 2,4-D and CW on embryogenesis

Figure 3:
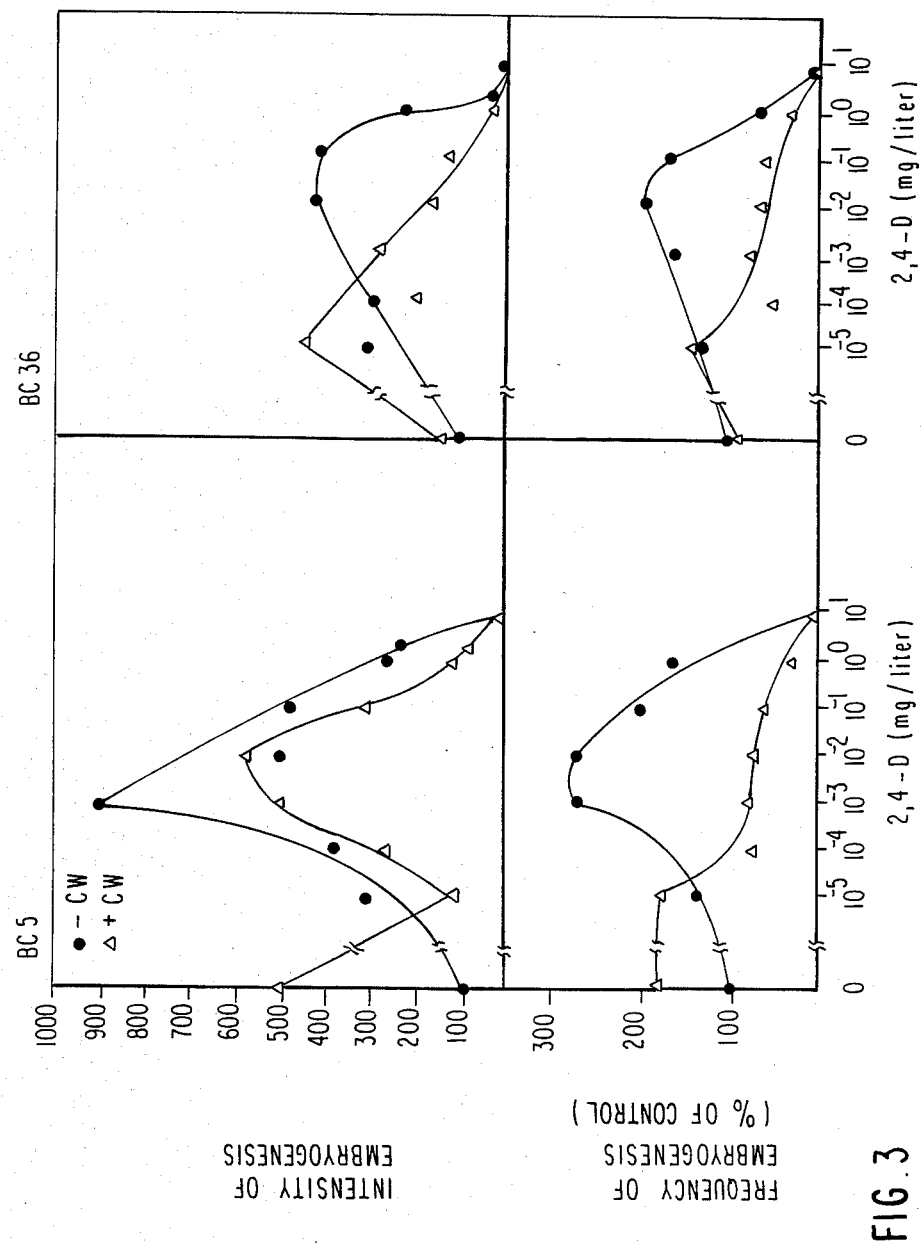
FIG. 3 is a graph showing the effect of 2,4-D and CW on asexual embryogenesis of clone BC 5 and clone BC 36 after six weeks.

In the absence of auxin and CW the yellow friable callus of both BC 5 and BC 36 formed occasional embryos (about 2 or 3 per explant) in about 30% of cultures. In the absence of CW, the frequency of embryogenesis increased with increasing concentrations of 2,4-D to a maximum response at $10^{-3}$ and $10^{-2}$ mg/liter for BC 5 and $10^{-2}$ for BC 36, and declined thereafter (FIG. 3). The intensity of embryogenesis (the number of embryos per culture) responded similarly to frequency (percent of culture with embryos). At the optimum response, intensity of embryos production increased almost 9 times that of the control with BC 5 and about 4 times with BC 36.

Coconut water alone increased embryogenesis over the control in callus BC 5 but not in BC 36. However, 2,4-D in the presence of CW suppressed embryogenesis above $10^{-5}$ mg/liter with the effect being proportional to the concentration tested. After 3 weeks many proembryos were observed in cultures supplemented with 2,4-D+CW but most of them died before developing into the torpedo stage. Coconut water alone increased the intensity of embryogenesis over the control with the greatest response in BC 5. However, 2,4-D in the presence of CW had a maximal effect on embryogenesis at $10^{-2}$ mg/liter for BC 5 and $10^{-5}$ mg/liter for BC 36.

These results suggest that the optimal hormonal conditions for embryogenesis of both clones were similar, differing only in detail. In general, the embryogenic response to 2,4-D and CW was greater in BC 5 than BC 36.

Histology of embryogenic callus

Figure 4:
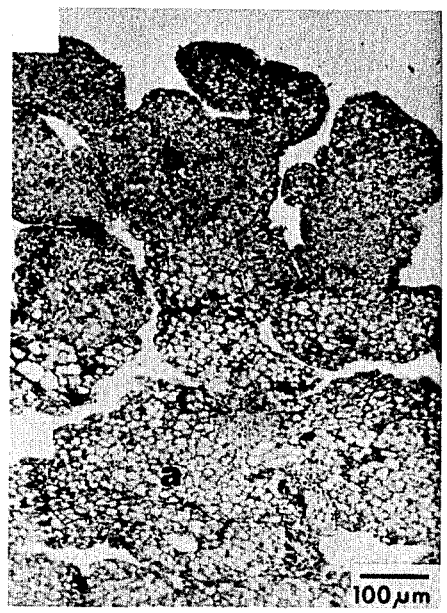
FIG. 4. Clone BC 5—Cross section of callus. The older portion is in the center (*a*) with new nodular growth (*b*) on the periphery. The younger growth is more intensely stained.
Figure 5:
FIG. 5. Clone BC 5—Close-up of older growth in FIG. 4(*a*). Note large cells with large vacuoles (*v*) and nucleus (*n*) with prominent nucleoli lying on the periphery of the cell.

Sections of the yellow Callus clumps revealed two distinct histological regions (FIG. 4). The central, inner region consisting of loose friable tissue was generally surrounded by compact nodular-like areas. The friable inner tissue (FIG. 5) was composed of large cells and disorganized areas of highly vacuolated, thick-walled cells ranging in size from 150–380 m$^2$. This inner region did not appear to be embryogenic.

Figure 6:
FIG. 6. Clone BC 5—Close-up of new growth in FIG. 4(*b*). Cells are small and compact with dense cytoplasm. Nuclei with prominent nucleoli are often in the middle and practically fill the entire cell.
Figure 15:
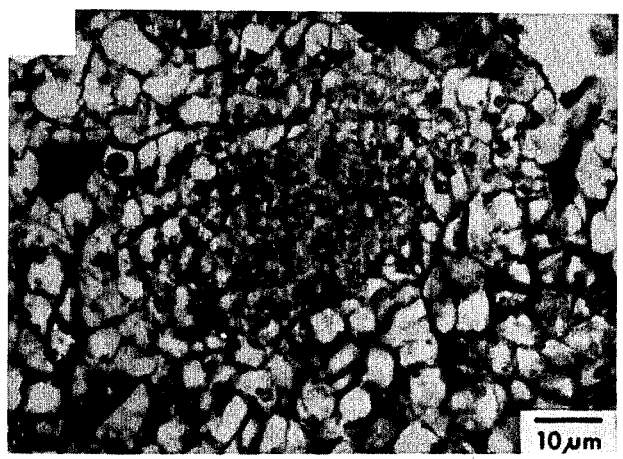
FIG. 15. Clone BC 5—Meristematic center surrounded by highly vacuolated cells.
Figure 16:
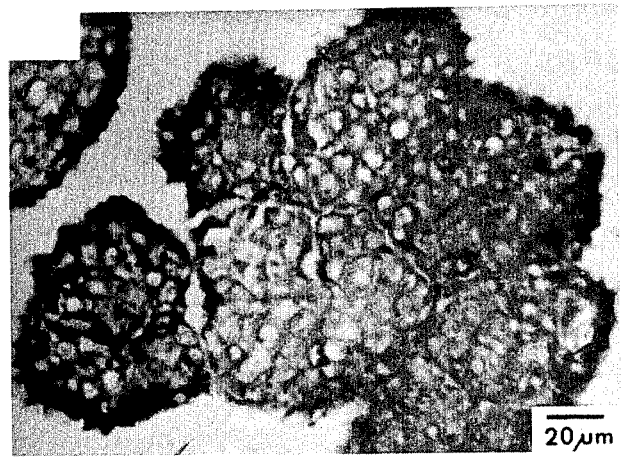
FIG. 16. Clone BC 5—Meristematic region showing fragmentation lines.

The peripheral, compact, nodular areas were multicellular structures composed of cells about 60–200 m$^2$ with thin walls and dense cytoplasm (FIG. 6). These cells had centrally positioned nuclei with prominent nucleoli. Cell divisions were restricted to these peripheral cells. Occasionally, centers of meristematic activity were found in the inner region among highly vacuolated cells (FIG. 15). The cytoplasm of dividing cells contained only small vacuoles or seemed to be unvacuolated. Asexual embryos (embryoids) originated from these meristematic nodules. This meristematic region had definite fragmentation lines which seemed to be formed by thickened cell walls (FIG. 16). These lines separated the smaller, meristematic cells from the surrounding larger, less-meristematic and more vacuolated cells within the agregates. During further growth of the meristematic agregates some of the cells that were most deeply embedded in the clumps become vacuolted. The peripheral cells remained unvacuolated and continued cycles of growth and fragmentation. Some of the meristematic clumps underwent differentiation to embryoids.

Development of somatic embryos from meristematic callus

Figure 7:
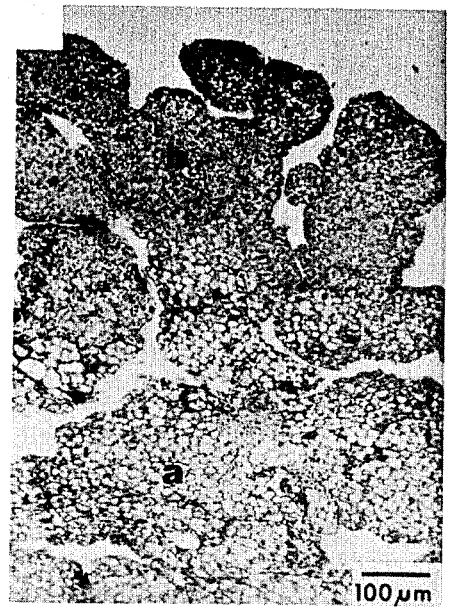
FIG. 7. Clone BC 5—A close-up of small compact spherical nodules in the new callus (see also FIG. 4(*b*). These compact nodules are loosely attached to one another and give the callus a friable texture. These nodular bodies resemble proembryos.
Figure 8:
FIG. 8. Clone BC 5—An older nodule showing an early stage of embryo (*e*) formation.
Figure 9:
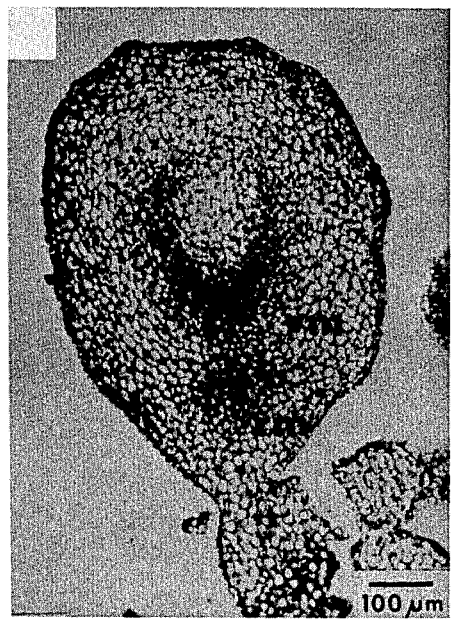
FIG. 9. Clone BC 5—Globular embryo showing the formation of root meristem (*rm*) and vascular meristem (*vm*).
Figure 10:
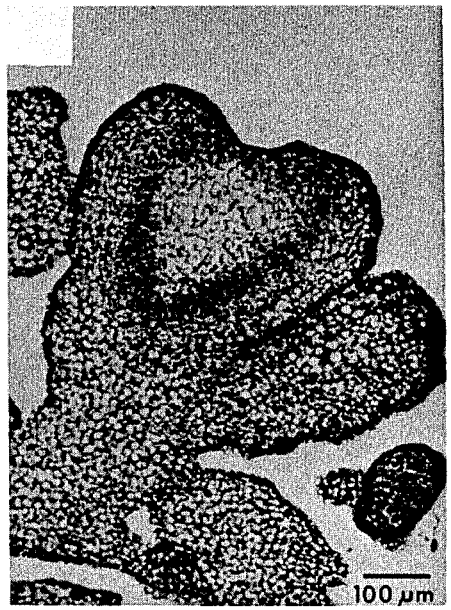
FIG. 10. Clone BC 5—Heart-shaped embryo stage connected to callus mass.
Figure 11:
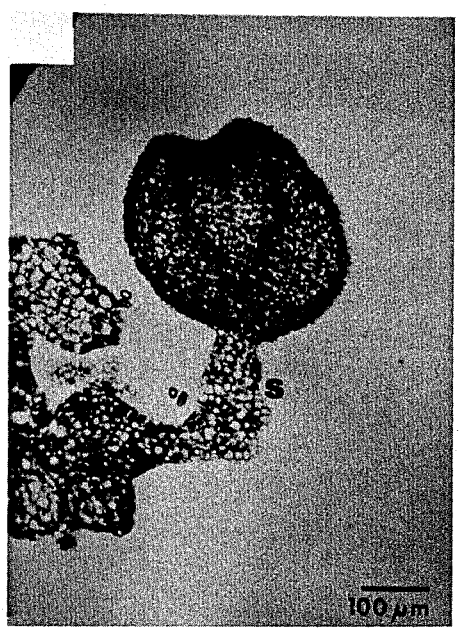
FIG. 11. Clone BC 5—Heart-shaped embryo with a suspensor-like connection(s) to the callus mass.
Figure 12:
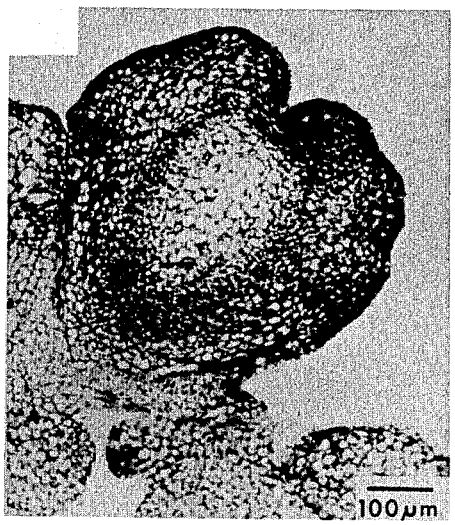
FIG. 12. Clone BC 5—Heart-shaped embryo loosely connected to the callus mass.
Figure 13:
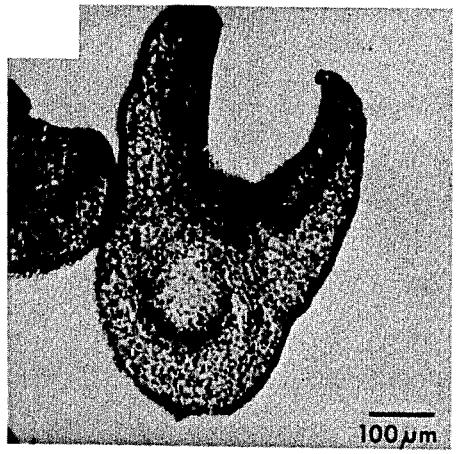
FIG. 13. Clone BC 5—Torpedo stage.
Figure 14:
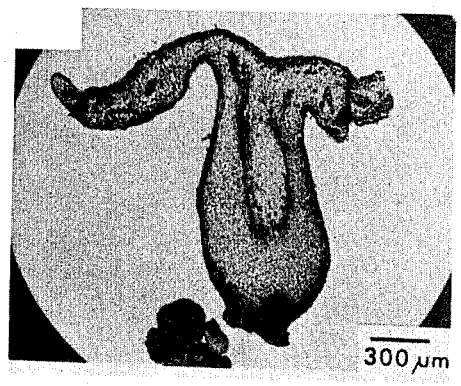
FIG. 14. Clone BC 5—"Walking stick" embryo stage showing cotyledonary development.

The sequence from small agregates of cells to the cotyledonary embryos was followed in BC 5. These small aggregates consisted of cells with large vacuoles (FIG. 7). The early stages of embryoid development showed no evidence of procambium (FIG. 7). The procambium appeared in the globular embryoid stage (FIGS. 8 and 9) and at this stage suspensor-like growths often appeared at the root end. Further stages of embryoid development are shown in FIGS. 10, 11, 12, 13, and 14). Heart-shaped embryoids (FIG. 10) contained procambium, root meristem, and rudimentary cotyledons. In some cases individual proembryoids were separated from the callus mass (FIG. 13), but in most cases individual embryoids remained embedded in the callus or were connected with parent bodies through suspensor-like structures (FIGS. 9 and 11). The cotyledon end emerged from the callus, while the root end of the embryoids remain in contact with the surrounding cells during globular, heart-shaped, and torpedo-shaped stages.

Figure 17:
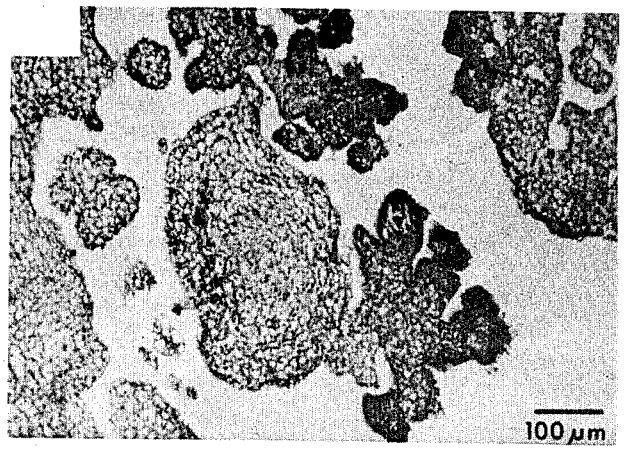
FIG. 17. Clone BC 36—Special embryo-like structures in an averted state of development with meristematic areas on embryogenesis occured at $10^{-3}$ to $10^{-2}$ mg/liter 2,4-D. Embryos originate from meristematic tissue at the periphery of callus clumps. Asexual embryos during development either remain embedded in the callus or are connected through suspensor-like structures.
Figure 18:
FIG. 18. Clone BC 36—Elongated embryo-like structures in an averted state of development with meristematic areas on the outer surface.

The developmental sequence of embryo formation from callus was similar for both clones but some abnormalities were observed in BC 36. BC 36 produced more meristematic centers than BC 5 but not all of them continued development. Most of these remained as spherical embryo-like structures which appeared to be in an arrested stage of development (FIG. 17). However, on the outer surface of these structures, further meristematic tissue formation commonly was observed (FIGS. 17 and 18).

Applicants have identified two clones of asexual embryos in *Theobroma cacao* L. that spontaneously produce embryos via callus on hormone-free medium. However, under this condition embryogenesis is typically of low frequency, being 1 or 2 developed embryos per callus explant. Our results indicate that embryogenic callus from these clones may be shifted toward homogeneous callus production with a combination of coconut water and 1 mg 2,4-D or to high frequency embryogenesis with 2,4-D alone at $10^{-3}$ to $10^{-2}$ mg/liter.

In our system in cacao with the 2 clones under investigation, exogenous auxin is not essential for the induction of embryos but low auxin stimulates embryogenesis. High auxin concentration, especially in the presence of CW, promotes callus formation.

Our results with callus suggest that CW alone stimulates asexual embryogenesis from callus, e.g. clone BC 5. But in general, a combination of CW+2,4-D depresses embryo initiation from callus.

We observed many globular structures in medium supplemented with CW and 2,4-D, but few developed beyond the torpedo stage. This suggests that CW in the presence of 2,4-D depresses embryo development at an early globular stage. Our results support Halperin's (1966) contention that CW is not absolutely required for the induction of embryogenic competence nor for the optimal expression of this competence.

Asexual embryos of *Theobroma cacao* from callus mass follow the normal pathway observed in developing zygotic embryos: i.e., globular, heart-shaped, torpedo-shaped, and finally cotyledonary (walking-stick) stage.

Histological evidence suggests that differences between direct and indirect embryogenesis occur in the early stages of development. In direct embryogenesis from hypocotylary budding, Pence et al (1980) recognized a 3-4 cell suspensor-like structure on which a 4 cell body is connected. In indirect embryogenesis the suspensor-like structure is variable in structure and usually not recognizable until the globular stage of embryo development. Subsequent development of direct and indirect embryogenesis follows the normal stages of zygotic embryo development, and from the product of further development of such embryos a cocoa butter-like product is obtained.

We claim:

1. A non-agricultural method for the production of cacao embryos comprising the steps of:
   (a) growing immature asexual or zygotic cacao embryos on a first basal medium until cotyledonary tissue which includes callus is produced;
   (b) separating the pre-determined embryogenic callus from the said cotyledonary tissue;
   (c) growing said callus on a second basal medium in the presence of a growth enhancer and continuing said callus growth through initiation and proliferation of cacao embryos.

2. The method of claim 1 in which selection of the embryogenic callus is made by choosing the friable tissue ranging from white to pale yellow in color.

3. The method according to claim 1 in which said callus is grown under low intensity illumination.

4. The method according to claim 3 in which said growth is done at about 26° C.

5. The method according to claim 1 in which the growth period according to step (C) is carried on for up to about 6 weeks.

6. The method according to claim 1 in which the growth enhancer is comprised of a dilute water solution containing 2,4-D.

7. The media of claim 1 in which the growth enhancer is coconut water.

8. The method of claim 1 in which the growth enhancer is a combination of a dilute water solution containing 2,4-D and coconut water.

9. The method of claim 1 in which the growth enhancer is the dilute water solution containing 2,4-D ranging in concentration from about between $10^{-3}$ and $10^{-2}$ mg/liter.

* * * * *